United States Patent
Goldberg et al.

(10) Patent No.: US 9,193,852 B2
(45) Date of Patent: Nov. 24, 2015

(54) STABLE AERATED COMPOSITIONS

(71) Applicant: L'OREAL, Paris (FR)

(72) Inventors: Andrew Goldberg, Clark, NJ (US);
Angelike Galdi, Westfield, NJ (US);
Raul M. Diaz, North Bergen, NJ (US)

( * ) Notice: Subject to any disclaimer, the term of this patent is extended or adjusted under 35 U.S.C. 154(b) by 0 days.

(21) Appl. No.: 14/141,534

(22) Filed: Dec. 27, 2013

(65) Prior Publication Data

US 2015/0183968 A1 Jul. 2, 2015

(51) Int. Cl.
*A61K 47/32* (2006.01)
*A61K 8/14* (2006.01)
*C08L 3/08* (2006.01)

(52) U.S. Cl.
CPC .................................. *C08L 3/08* (2013.01)

(58) Field of Classification Search
USPC ................. 424/448, 449, 486, 488, 401; 514/772.3, 772.4
See application file for complete search history.

(56) References Cited

U.S. PATENT DOCUMENTS 6,251,954 B1  6/2001  Roulier et al.
6,605,290 B2  8/2003  Roulier et al.

FOREIGN PATENT DOCUMENTS

| DE | 10229812 A1 | 1/2004 | |
| EP | 1046387 A1 | 10/2000 | |
| EP | 1 925 282 A2 * | 5/2008 | ............... A61K 8/04 |
| EP | 1925282 A2 | 5/2008 | |
| JP | 56079613 A | 6/1981 | |
| WO | 94/12145 A2 | 6/1994 | |
| WO | 2011109469 A1 | 9/2011 | |

* cited by examiner

*Primary Examiner* — Robert Harlan

(57) ABSTRACT

The present invention is directed to an aerated composition comprising, in a physiologically acceptable medium, an oily phase dispersed in an aqueous phase, characterized in that it contains air or inert gas in a sufficient amount to have a relative density ranging from about 0.2 to about 0.9 (g/cm$^3$) measured at a temperature of approximately 25° C. and at atmospheric pressure, and in that it comprises at least one modified starch, at least one emulsifier, and at least one oil-dispersible structuring agent.

15 Claims, No Drawings

STABLE AERATED COMPOSITIONS

BACKGROUND OF THE INVENTION

Creams are conventionally composed of an emulsion. Emulsions comprise an aqueous phase and an oily phase dispersed in one another. Oil-in-water (O/W) emulsions, the external phase of which is the aqueous phase, are more particularly desired because they contribute more freshness on application than water-in-oil (W/O) emulsions comprising an oily external phase. Their feel and their application seem to be less greasy than those of a W/O emulsion. In addition, they make possible a high level of moisturizing, which is particularly useful in caring for dry skin or lips.

In order to confer a novel texture on emulsions, attempts have been made to introduce a gas, generally air, therein in order to confer on them a light texture and to give them the appearance of foam. This is what is known as aeration. The aerated emulsions obtained are appreciated for their lightness on skin feel and ease of application, more specifically on ease of spreadability without dragginess. Nevertheless, they exhibit the disadvantage of being relatively unstable because of their low relative density and thus of separating out after a certain storage time. The document CH-A-674,804 discloses stabilization of an aerated cosmetic cream comprising an inert gas or air by the addition of an aqueous solution of a protein of animal origin. However, the use of such proteins is avoided in cosmetics.

Furthermore, the document JP-A-56/079613 discloses stable aerated surfactant-free compositions comprising from 5 to 20% of waxes, preferably waxes with a high melting point. The emulsions obtained are then stable but exhibit cosmetic properties which are unacceptable to the user. This is because these compositions comprise very little water and therefore lack freshness when applied to the skin. In addition, they comprise a significant amount of humectants, such as glycerol, which leads to a feeling of stickiness to the touch. In addition, the use of a wax with a high melting point in an amount of 5% results in heavy textures which are very difficult to apply to the skin.

The need thus remains for an emulsion which has the appearance of foam, while comprising a large amount of water, and which is fresh and not sticky when applied to the skin.

BRIEF SUMMARY OF THE INVENTION

The present invention is directed to an aerated composition comprising, in a physiologically acceptable medium, an oily phase dispersed in an aqueous phase, characterized in that it contains air or inert gas in a sufficient amount to have a relative density ranging from about 0.2 to about 0.9 (g/cm$^3$) measured at a temperature of approximately 25° C. and at atmospheric pressure, and in that it comprises at least one modified starch, at least one emulsifier, and at least one oil-dispersible structuring agent.

DETAILED DESCRIPTION OF THE INVENTION

Other than in the operating examples, or where otherwise indicated, all numbers expressing quantities of ingredients and reaction conditions are to be understood as being modified in all instances by the term "about".

The composition of the invention exhibits a relative density which is lower than that of a conventional emulsion and yet nevertheless remains very stable over time. The aerated composition of the invention comprises air or inert gas bubbles and has a relative density ranging from about 0.2 to about 0.9 (g/cm$^3$) and preferably from about 0.4 to about 0.8, this relative density being measured at a temperature of approximately 25° C. and at atmospheric pressure.

Inert gas may be nitrogen, helium or argon. The amount of air or inert gas necessary to obtain the wanted density is of at least 30% by volume, and it may range for example from 40 to 80% by volume, and preferably from 50 to 70% by volume with respect to the total volume of the composition.

The composition of the invention differs from foams obtained with a propellant (such as isobutane), such as shaving foams, by the fact that it stays as a stable foam over time, contrary to shaving foams which break down very quickly.

The composition of the invention advantageously comprises a physiologically acceptable medium, that is to say compatible with the skin, eyes and/or hair, and it can constitute in particular a cosmetic and/or dermatological composition.

This composition is an O/W (oil-in-water) emulsion which is neither greasy nor heavy and, as the external phase is the aqueous phase, it gives an impression of freshness on application to the skin.

Modified Starch

The composition of the invention comprises at least one modified starch. The modified starches should possess a yield strength, measured in solution, ranging from about 2% to about 6%, preferably from about 3% to about 5%, and most preferably from about 3.5% to about 4.5%.

Particularly preferred modified starches for use in the present invention are starch phosphates such as:

monostarch phosphates of formula (I),

  Am—O—PO—(OX)$_2$   (I)

distarch phosphates of formula (II),

  Am—O—PO—(OX)—O—Am   (II)

tristarch phosphates of the formula (III),

  Am—O—PO—(O—Am)$_2$   (III)

and mixtures thereof,
wherein:
Am represents starch;
X represents alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

Particularly suitable starch phosphates which may be employed include, but are not limited to, hydroxypropyl starch phosphate, starch acetate, sodium tripolyphosphate, sodium orthophosphate, phosphorus oxychloride or sodium trimetaphosphate, and mixtures thereof.

A particularly preferred modified starch for use in the present invention is hydroxypropyl starch phosphate.

The composition of the invention generally comprises an amount of modified starch ranging from about 2 to about 8% by weight, preferably from about 3 to about 7% by weight, and most preferably from about 4 to about 6% by weight, all weights based on the total weight of the composition.

Emulsifiers

The composition according to the invention additionally comprises an emulsifier conventionally used for O/W emulsions which is preferably nonionic.

Suitable emulsifiers include, for example:
(1) nonionic surfactants having an HLB of greater than or equal to 9, such as oxyethylenated esters of a fatty acid and of glycerol; oxyethylenated esters of a fatty acid and of sorbitan; oxyethylenated derivatives of a fatty acid; esters of a fatty acid and of a sugar and in particular sucrose fatty esters, such as sucrose stearate, for example the product sold under the name TEGOSOFT® PSE 141 G by the company Evonik-Goldschmidt; alkyl polyglucoside ethers; PEG-100 stearate; and their mixtures;
(2) silicone emulsifiers, such as oxyethylenated polydimethylmethylsiloxanes (dimethicone copolyol), such as, for example, that sold under the name "DC2-5695" by the company Dow Corning.

The composition according to the invention contains from about 0.5 to about 5% by weight, preferably from about 1 to about 4% by weight, and better still from about 1 to about 3% by weight of emulsifier(s), all weights being based on the total weight of the composition.

Oily Phase

The nature of the oily phase of the emulsion according to the invention is not critical. The oily phase can thus be composed of any fatty substance, in particular oils, conventionally used in the cosmetic and dermatological fields.

Mention may be made, among oils which can be used in the composition of the invention, of, for example, vegetable oils, such as apricot oil, mineral oils, such as liquid petrolatum, synthetic oils, such as isohexadecane; volatile or non-volatile silicon oils; and fluorinated oils. Mention may in particular be made, as volatile silicone oils, of cyclic polydimethylsiloxanes or cyclomethicones which comprise from approximately 3 to 9 silicon atoms and preferably from 4 to 6 silicon atoms, such as cyclohexadimethylsiloxane, cyclopentadimethylsiloxane and/or cyclotetradimethylsiloxane, also commonly referred to as cyclotetrasiloxane and combinations thereof. The other fatty substances capable of being present in the oily phase can be, for example, fatty acids, fatty alcohols, such as cetyl alcohol, and waxes.

The composition according to the invention advantageously comprises from about 1 to about 40% by weight, preferably from about 10 to about 30% by weight, and better still from about 15 to about 25% by weight of oily phase, all weights being based on the total weight of the composition.

Thickeners

The composition of the present invention further includes at least one thickener. Suitable thickeners include, but are not limited to, water-dispersible polysaccharides such as xanthan gum, guar gum, biosaccharide gum, cellulose, acacia Seneca gum, sclerotium gum, agarose, pechtin, gellan gum, hyaluronic acid; polymeric thickeners such as ammonium polyacryloyldimethyl taurate, ammonium acryloyldimethyltaurate/VP copolymer, sodium polyacrylate, acrylates copolymers, polyacrylamide, carbomer, acrylates/C10-30 alkyl acrylate crosspolymer, and mixtures thereof.

Particularly preferred thickeners for use in the present invention include xanthan gum and ammonium polyacryloyldimethyl taurate.

The composition of the present invention will typically contain the thickener in an amount of from about 0.2 to about 3% by weight, preferably from about 0.4 to about 2% by weight, and most preferably in an amount of from about 0.5 to about 1.5% by weight, all weights being based on the total weight of the composition.

Oil-Dispersible Structuring Agent

The composition of the present invention further includes at least one oil-dispersible structuring agent. Examples of suitable oil-dispersible structuring agents include glyceryl stearate, rhea butter, hydrogenated jojoba oil, cocoa butter, cetyl alcohol, stearyl alcohol (or any other mid range-C alkyl chain, beeswax, carnuba wax, candelilla wax, cetyl dimethicone and mixtures thereof.

The composition of the present invention will typically contain the oil-dispersible structuring agent in an amount of from about 2 to about 15% by weight, preferably from about 5 to about 12% by weight, and most preferably in an amount of from about 7 to about 9% by weight, all weights being based on the total weight of the composition.

Aqueous Phase

The aqueous phase of the emulsion constituting the composition of the invention can represent from 15 to 97.95% by weight, preferably from 57 to 93% and better still from 75 to 90% by weight with respect to the total weight of the composition.

Adjuvants

In a known way, the composition of the invention can also comprise adjuvants typically employed in the cosmetics field, such as active, humectants, preservatives, antioxidants, complexing agents, solvents, fragrances, screening agents, bactericides, odour absorbers, colouring materials (pigments or soluble dyes) and lipid vesicles. The amounts of these various adjuvants are those conventionally used in the field under consideration, for example from 0.01 to 20% of the total weight of the composition. These adjuvants, according to their nature, can be introduced into the fatty phase, into the aqueous and/or into the lipid vesicles.

The present invention also relates to the process for the manufacture of the composition according to the invention. This process involves preparing the emulsion in a conventional way by introducing the oily phase into the aqueous phase with stirring, for example in a device of Moritz type, and in then introducing air into the emulsion obtained with mixing ranging from 500 to 1500 revolutions/minute, at a temperature ranging from 20° C. to 80° C. and preferably at about room temperature, under an air inlet pressure ranging from about 7 to 10 bar ($7 \times 10^5$ á $1 \times 10^6$ Pa) and preferably from 8 to 9 bar ($8 \times 10^5$ á $9 \times 10^5$ Pa).

Another embodiment of the present invention is therefore related to a process for the manufacture of an aerated composition based on an oil-in-water emulsion which comprises:
(1) preparing an oil-in-water emulsion containing at least one modified starch, at least one emulsifier, at least one thickener, at least one oil-dispersible structuring agent, in a conventional way by dispersing the oily phase in the aqueous phase,
(2) in introducing air into the emulsion obtained with stirring ranging from 500 to 1500 revolutions/minute, at a temperature ranging from 20° C. to 80° C., preferably about room temperature and under an air inlet pressure ranging from about 7 to 10 bar.

According to a preferred embodiment of the invention, the introduction of the air into the emulsion is carried out in an aeration device comprising a mixing head comprising a rotor and a stator, such as, for example, the "Minimondo-type Mondomixer" supplied by the company Mondomix.

The composition according to the invention is applied in a large number of treatments, in particular cosmetic treatments, of the skin, the lips and hair, including the scalp, in particular for treating, protecting, caring for, removing make-up from and/or cleansing the skin, lips and/or hair and/or for making up the skin and/or lips.

EXAMPLES

The examples below are illustrative only and are not intended to unduly limit the scope of the invention in any way.

TABLE 1

| | | Examples | | | |
|---|---|---|---|---|---|
| | | Inventive | Comparative | | |
| Phase | US INCI NAME | Ex. 1 | Ex. 2 | Ex. 3 | Ex. 4 |
| A1 | WATER, PRESERVATIVES | QS 100 | QS 100 | QS 100 | QS 100 |
| A1 | GLYCERIN | 10 | 10 | 10 | 10 |
| A1 | DISODIUM EDTA | 0.1 | 0.2 | 0.2 | 0.1 |
| A2 | HYDROXYPROPYL STARCH PHOSPHATE | 4.4 | | | 4.4 |
| A2 | XANTHAN GUM | 0.2 | 0.2 | 0.2 | 0.2 |
| B | CAPRYLIC/CAPRIC TRIGLYCERIDE | 10 | 10 | 10 | 10 |
| B | BUTYROSPERMUM PARKII (SHEA) BUTTER | 2.5 | 2.5 | 2.5 | 2.5 |
| B | DICAPRYLYL ETHER | 2.5 | 2.5 | 2.5 | 2.5 |
| B | STEARYL ALCOHOL | | 2 | 2 | |
| B | GLYCERYL STEARATE | 5 | | | 5 |
| B | GLYCERYL STEARATE (and) PEG-100 STEARATE (50/50) | 2 | 2 | 2 | 2 |
| C | AMMONIUM ACRYLOYLDIMETHYLTAURATE/VP COPOLYMER | | 1.43 | 1.43 | |
| C | AMMONIUM POLYACRYLOYLDIMETHYL TAURATE | 0.97 | | | |
| D | TOCOPHERYL ACETATE | 0.2 | 0.2 | 0.2 | 0.2 |
| E | ALCOHOL DENAT. | 3 | 3 | 3 | 3 |
| E | CAPRYLOYL SALICYLIC ACID | 0.1 | 0.1 | 0.1 | 0.1 |
| F | NYLON-66 | | 5 | | |
| G | pH ADJUSTERS | | Adjust to pH = 5.3 | Adjust to pH = 5.3 | |
| | Viscosity (UD, spindle 4) | 43 | 17 | 10 | <10 |
| | Visual Appearance | Whipped | Whipped | Not Whipped | Too Thin |
| | Density, initial pre-aeration, (g/mL) | 0.94 | 0.85 | 0.96 | 0.98 |
| | Density, initial post-aeration, (g/mL) | 0.73 | 0.72 | 0.78 | not tested |
| | Density, T1M, 45° C., (g/mL) | 0.88 | Very Thick | Very Thick | not tested |
| | Density, T2M, 45° C., (g/mL) | 0.92 | Very Thick | Very Thick | not tested |
| | Stability | Stable | Stable | Stable | Stable |

In making each of the examples in Table 1, the following procedure was used:

The ingredients of Phase A1 were mixed together in the main kettle and heated to 75. Once the mixture was homogenous, phase A2 was added with mixing. The mixing speed was increased until all the ingredients were dispersed. The ingredients of phase B were combined in a side beaker and heated to 75° C. Phase B was added to the main kettle. The contents of the main kettle were emulsified, and cooling was begun. The ingredients of phase C were added to the main kettle with mixing until dispersed. Phase D was added to the main kettle once the kettle contents reached 40° C. The ingredients of phase E were combined in a side beaker until fully dissolved. Phase E was added to the main kettle once the kettle contents reached 30° C. Phase F, if employed, was added to the main kettle with mixing. Phase C, if employed, was used to adjust the pH. The above-identified compositions were then run through a Mondomix apparatus for aeration.

Density of the final aerated composition was measured with a pycnometer. The cup and lid were zeroed on the scale then filled with the product. Excess was wiped away and the mass of the sample in the cup was observed. The mass was multiplied by the factor 0.1202 to obtain the specific gravity, in q/mL.

Viscosity was measured at 25° C. using a Rheomat 180 equipped with a spindle rotating after 10 minutes at 200 rpm. Those skilled in the art may select the spindle for measuring the viscosity from spindles M3 or M4 on the basis of their general knowledge, so as to be able to perform the measurement.

The final aerated composition should possess a density, as measured per the above description, ranging from about 0.5 to about 0.9 g/ml, preferably from about 0.55 to about 0.85 g/ml, and most preferably from about 0.6 to about 0.8 g/ml.

What is claimed is:

1. A composition comprising:
   (a) At least one starch phosphate;
   (b) At least one emulsifier;
   (c) An oil phase;
   (d) At least one thickener;
   (e) At least one oil-dispersible structuring agent; and
   (f) An aqueous phase,
wherein the composition is aerated with air and/or an inert gas.

2. The composition of claim 1 wherein (a) is a hydroxypropyl starch phosphate.

3. The composition of claim 1 wherein (a) is present in the composition in an amount of from about 2 to about 8% by weight, based on the total weight of the composition.

4. The composition of claim 1 wherein (a) is present in the composition in an amount of from about 3 to about 7% by weight, based on the total weight of the composition.

5. The composition of claim 1 wherein (b) is a nonionic emulsifier.

6. The composition of claim 1 wherein (b) is present in the composition in an amount of from about 0.5 to about 5% by weight, based on the total weight of the composition.

7. The composition of claim 1 wherein (b) is present in the composition in an amount of from about 1 to about 3% by weight, based on the total weight of the composition.

8. The composition of claim 1 wherein (d) is ammonium polyacryloyldimethyl taurate.

9. The composition of claim 1 wherein (d) is present in the composition in an amount of from about 0.2 to about 3% by weight, based on the total weight of the composition.

10. The composition of claim 1 wherein (d) is present in the composition in an amount of from about 0.4 to about 2% by weight, based on the total weight of the composition.

11. The composition of claim 1 wherein (e) is present in the composition in an amount of from about 2 to about 15% by weight, based on the total weight of the composition.

12. The composition of claim 1 wherein (e) is present in the composition in an amount of from about 5 to about 12% by weight, based on the total weight of the composition.

13. The composition of claim 1 wherein the composition has a density ranging from about 0.9 to about 0.5 g/ml.

14. The composition of claim 1 wherein the composition has a density ranging from about 0.85 to about 0.55 g/ml.

15. A composition comprising:
  (a) From about 4 to about 6% by weight of a hydroxypropyl starch phosphate;
  (b) From about 1 to about 3% by weight of a nonionic emulsifier;
  (c) An oil phase;
  (d) From about 0.5 to about 1.5% by weight of an ammonium polyacryloyldimethyl taurate;
  (e) From about 7 to about 9% by weight of at least one oil-dispersible structuring agent; and
  (f) An aqueous phase,
  wherein the composition is aerated with air and/or an inert gas and wherein the composition has a density of from about 0.6 to about 0.8 g/ml.

\* \* \* \* \*